US00PP11246P

United States Patent [19]

Weigall

[11] Patent Number: Plant 11,246

[45] Date of Patent: Feb. 29, 2000

[54] NAVEL ORANGE TREE NAMED 'WIFFEN SUMMER NAVEL'

[75] Inventor: Andrew Weigall, Renmark, Australia

[73] Assignee: Yandilla Park Ltd., Renmark, Australia

[21] Appl. No.: 08/880,231

[22] Filed: Jun. 23, 1997

[51] Int. Cl.[7] ..... A01H 5/00

[52] U.S. Cl. ..... Plt./202

[58] Field of Search ..... Plt./45, 201, 202

[56] References Cited

U.S. PATENT DOCUMENTS

P.P. 6,733 4/1989 Powell et al. ..... Plt./202

P.P. 7,651 9/1991 McLaren ..... Plt./202

P.P. 9,241 8/1995 Green ..... Plt./45

*Primary Examiner*—Howard J. Locker

*Attorney, Agent, or Firm*—Townsend and Townsend and Crew LLP

[57] ABSTRACT

The invention provides for a novel navel orange tree named Wiffen Summer Navel. It is characterized by a later fruit maturity in comparison with other later navel varieties, such as the Lane Late navel varieties.

1 Drawing Sheet

BACKGROUND OF THE INVENTION

This invention relates to a novel variety of navel orange tree. The invention is characterized by relative late maturity of its fruit in comparison with other known late navel varieties, such as the Lane Late navel varieties. The varietal information as it relates to taxonomically important seasonal information was determined for Australia which is in the southern hemisphere. All time periods remain essentially unchanged in the northern hemisphere, but the time frame is shifted by approximately six months. Therefore, activities in April or May would correspond in the U.S. to activities in October or November.

The plant is of unknown parentage and was found as a young tree in an orchard of valencia orange trees in Nangiloc in Victoria, Australia in 1987. Although the plant flowered at the same time as other navel oranges, the fruit matured later than any of the other commercially available varieties including Lane Late. The plant maximally flowers in mid October and provides mature fruit from November to February. The typical navel orange matures in September and October and late varieties mature in November and December. Wiffen Summer Navel is the first variety to our knowledge that will meaningfully extend the navel season into February. Navel oranges are a significant fresh fruit crop and there are economic advantages to extending its availability to consumers.

The variety Lane Late is believed to be the variety which is closest to Wiffen Summer Navel in phenotype. However, Wiffen Summer Navel differs from Lane Late in three important characteristics. The Wiffen Summer Navel fruits mature later, the total soluble solids of mature Wiffen Summer Navel fruit is greater (better flavor) and the Wiffen Summer Navel fruit are smaller. In side-by-side trials against late hanging varieties, Rohde Summer Navel (U.S. Plant Pat. No. 7,651), Powell (U.S. Plant Pat. No. 6,733), Summer Gold, Hutton, Christensen and Autumn Gold, Wiffen Summer Navel has the highest total solids, the highest acid content, and smallest average size (see Gallasch, P. T., Int'l Citrus Congress, May 1996, *The Proceedings of the International Society of Citriculture* (*In Press*)). In all other regards, The Wiffen Summer Navel variety falls within the standards for commercially acceptable navel oranges.

Wiffen Summer Navel has been asexually reproduced by grafting trees 11 and 16 and has been determined to be stable. The following data was taken from two eight year old plants which have been grafted onto a sweet orange interstock and rootstock (Citrange). The location was Victoria, Australia, at the Sunraysia Horticulture Centre.

DESCRIPTION OF THE DRAWINGS

The accompanying photographs show the tree and fruit of the present invention. In such photographs.

DETAILED DESCRIPTION OF THE PLANT

Figure 1:
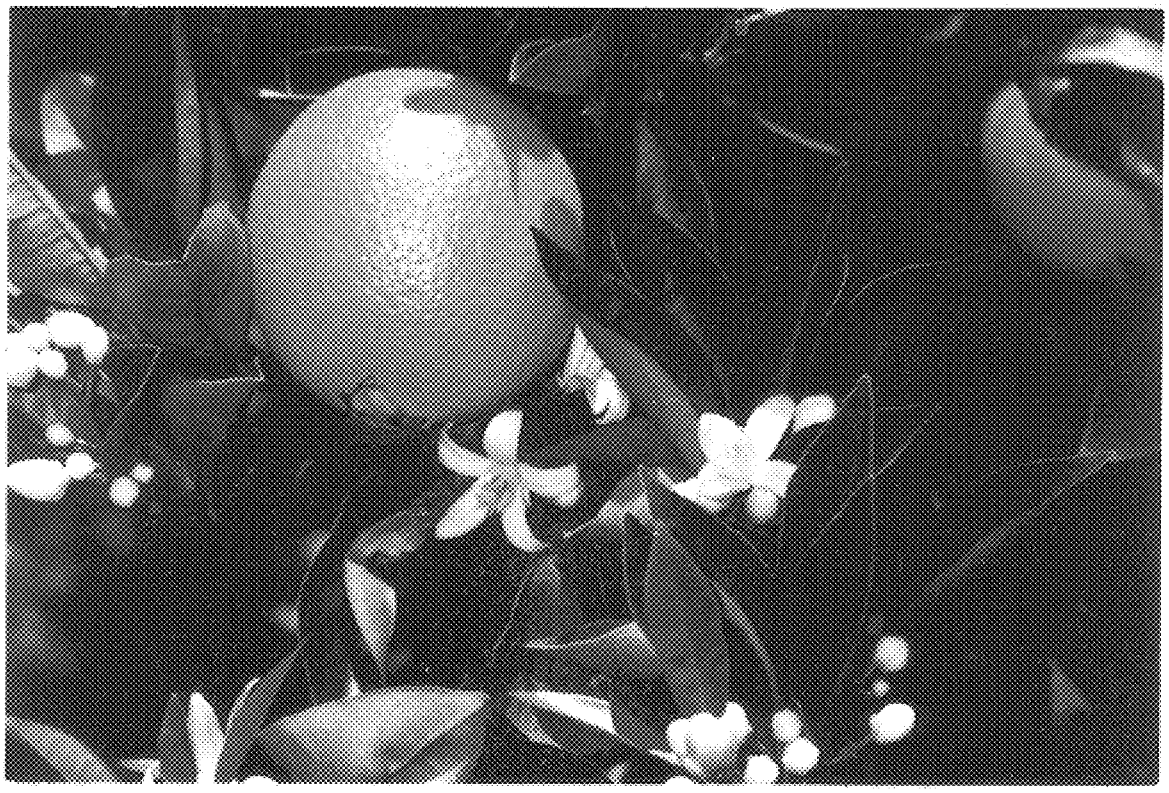
FIG. 1 shows the fruit of 'Wiffen Summer Navel'.
Figure 2:
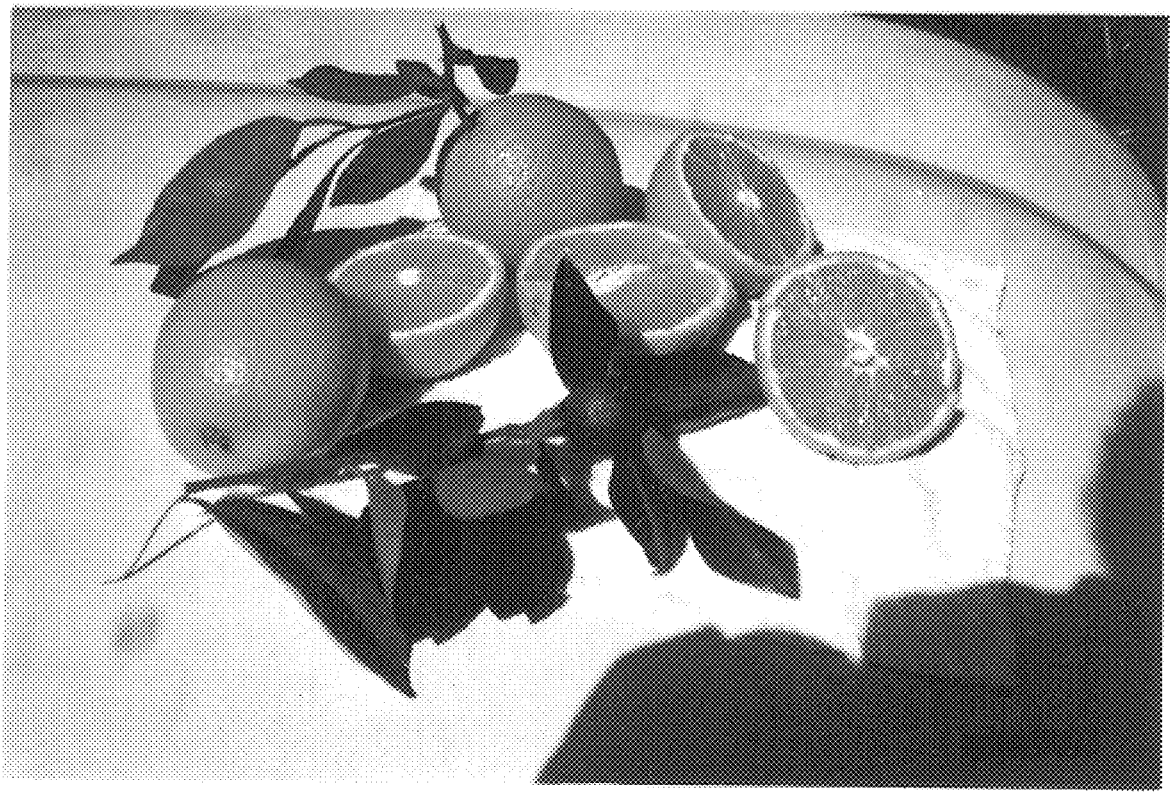
FIG. 2 shows the cross-sectional view of the fruit of 'Wiffen Summer Navel'.

The following is an outline description in greater detail of the new and distinct variety of navel orange tree of the present invention. All specific color designations set forth are determined from the R.H.S. Colour Chart:

GENERAL INFORMATION

*Species.*—*Citrus sinensis.*
*Variety*—Navel orange.
*Strain.*—Wiffen Summer Navel.
*Location.*—Victoria.
*Grove.*—Sunraysia Horticultural Centre.
*Plot.*—Old sprinkler trial area.
*Row.*—2.
*Trees.*—11 and 16.
*Fruit maturiey season.*—Approximately November–February.
*Use.*—Fresh fruit variety.
*Fruit weight.*—251 to 292 grams average/100 randomly sampled fruit.

Bloom:
*Date maximum.*—October 11.
*Distribution.*—Uneven, Abundant.
*Flower.*—Mostly clustered flowers with some single flowers (approx. 20%), medium sized.
*Aroma.*—Present and typical for navel oranges.
*Petal color.*—155D(R.H.S.).
*Stamens.*—Number an average of 24.6.

*Floral defects.*—No pollen produced.
*Anther color.*—162A and 162B (R.H.S.).

EXTERNAL CHARACTERISTICS

Fruit: Wiffen Summer Navel regreens in a similar manner as all oranges exposed to hotter weather. Wiffen Summer Navel stores well on the tree in a manner similar to other late hanging navel oranges.
*Date fruit set.*—November 20th.
*Distribution of fruit.*—Outside of tree.
*Commercial quality.*—High.
*Form.*—Globose to ovoid.
*Base.*—Even rounded.
*Apex.*—Rounded.
*Navel characteristics.*—Small, open.
*Navel occurrence.*—One per fruit.
*Navel size.*—Diameter of 9 mm.
*Diameter of fruit.*—7.42 cm.
*Length of fruit.*—8.00 cm.
Stem:
*Size.*—Average length is 4.7 cm.
*Color.*—Dark green.
*Position.*—Straight.
*Calyx.*—Even.
*Sepals.*—Acute. 4–5 in number.
Rind:
*Adherent to pulp.*—Close.
*Surface.*—Grained.
*Color.*—Orange color=23A (R.H.S.); Green color=145A (R.H.S.).
*Aroma.*—Medium.
Rind oil cells: Small, even;
*Color.*—Orange; No. per $cm^2$: 106.
Longitudinal section of fruit:
*Rind thickness.*—7.9 mm apex; 5.7 mm median, 5.7 mm base.
*Oil cells.*—Shape-round; No. per $cm^2$. 106.
Fruit quality:
*Color.*—Orange; Oil: slight.
*Aroma.*—Medium.
*Albedo.*—Color — white, medium.
*Thickness of albedo.*—3.9 mm.
*Taste.*—Sweet, good.
*Adherence of rind to pulp.*—Medium.
*Puffing.*—None.
*Fruit axis.*—Straight.
*Hollowness.*—Solid.
Cross section:
*Number of segments.*—10.5.
*Shape.*—Variable.
*Periphery angle.*—Medium.
*Periphery center.*—Slight.
*Separation.*—Medium.
*Segment apical shape.*—Rounded.
*Vascular bundles.*—Scarce, yellow.
*Septa.*—Thin, medium.
*Columella diameter.*—1.2 cm.
Flesh:
*Color.*—25A (R.H.S.).
*Ridgeway.*—Uniform, light.
*Texture.*—Fine, tender.
*Vesicles.*—Medium.
*Size.*—Width 70.9 mm.
*Length.*—67.8 mm.
*Uneven granulation.*—Not present.
Juice:
*Amount.*—60%; juicy.
*Sugar.*—12.8 degrees Brix.
*Total soluble solids.*—76.3 kg/ton.
*Acid.*—0.49 g/100 ml.
*Bitterness.*—None.
*Aroma.*—Medium.
*Flavor.*—Sweet, sugar and acid well blended.
*Quality.*—Good.
Seeds: Absent.
Tree: Average production in year 5 is 2.5 tonnes per hectare. In year six, production is 12 tonnes per hectare. At full maturity, the trees produce in excess of 30 tonnes per hectare. Daughter trees grown 200 kilometers from the parent tree have shown the same characteristics as the parent tree.
*Age.*—8 years, reworked onto sweet orange interstock and rootstock.
*Vigor.*—Medium; Height: 3 meters.
*Spread.*—3.0 meters.
*Habit of growth.*—Spreading intermediate.
*Thorns.*—Absent.
*New wood color.*—143C (R.H.S.).
*Mature wood color.*—193C (R.H.S.).
Trunk:
*Height of union.*—High.
*Scion.*—Even.
*Bark.*—Smooth.
*Color.*—Brown.
Head:
*Height from ground.*—1.8 meter.
*Branches.*—Irregular, vase.
*Shape of limbs.*—Rounded.
Root system: Dependent on rootstock.
Leaves: Many, smooth, simple.
*Length.*—62.3 mm.
*Width.*—24.3 mm.
*Oil cells.*—29.28 per square centimeter.
*Color.*—Upper surface glossy dark green, no deficiencies or toxicity present.
*Lower surface.*—Dark green.
*Shape.*—Uniform, elliptical.
*Base.*—Rounded.
*Apex.*—Acute,entire.
*Margin.*—Entire.
*Marginal oil cells.*—Few.
*Petiole.*—Winged.
*Wing width.*—2 mm.
*Wings.*—2.

SUSCEPTIBILITY

To insects: Average.
To diseases: Average.
Physiological characteristics: Up to 20% of fruit can drop in Spring if subjected to environmental stress, e.g., water stress.

The tree and its fruit as described herein may vary in slight detail due to climatic or soil conditions under which the variety is grown.

What is claimed is:

1. A new and distinct variety of navel orange tree substantially as shown and described, characterized particularly as to novelty by a relatively late maturing fruit in comparison with other known late navel varieties.

* * * * *